United States Patent [19]

Thalen et al.

[11] 4,404,200

[45] Sep. 13, 1983

[54] 4-PREGNENE-DERIVATIVES, A PROCESS FOR THEIR PREPARATION, COMPOSITION AND METHOD FOR THE TREATMENT OF INFLAMMATORY CONDITIONS

[75] Inventors: Bror A. Thalen, Bjärred; Ralph L. Brattsand, Lund, both of Sweden

[73] Assignee: Aktiebolaget Draco, Lund, Sweden

[21] Appl. No.: 322,592

[22] Filed: Nov. 17, 1981

[30] Foreign Application Priority Data

Dec. 4, 1980 [SE] Sweden .................................. 8008524

[51] Int. Cl.³ ............................................. A61K 31/58
[52] U.S. Cl. ............................ 424/241; 260/239.55 D
[58] Field of Search ................ 424/241; 260/239.55 D

[56] References Cited

U.S. PATENT DOCUMENTS

| | | | |
|---|---|---|---|
| 2,990,401 | 6/1961 | Bernstein et al. | 260/239.55 D |
| 3,048,581 | 8/1962 | Fried | 260/239.55 D |
| 3,549,498 | 12/1970 | Diassi et al. | 260/239.55 D |
| 3,928,326 | 12/1975 | Brattsand et al. | 260/239.55 D |
| 3,996,359 | 12/1976 | Brattsand et al. | 260/239.55 D |

FOREIGN PATENT DOCUMENTS

| | | | |
|---|---|---|---|
| 2016353 | 5/1971 | Fed. Rep. of Germany | 260/239.55 D |
| 487089 | 12/1979 | Spain | 260/239.55 D |
| 378110 | 8/1975 | Sweden | 260/239.55 D |
| 909126 | 3/1959 | United Kingdom | 260/239.55 D |

*Primary Examiner*—Elbert L. Roberts
*Attorney, Agent, or Firm*—Brumbaugh, Graves, Donohue & Raymond

[57] ABSTRACT

The invention refers to compounds having anti-inflammatory activity, characterized by the formula

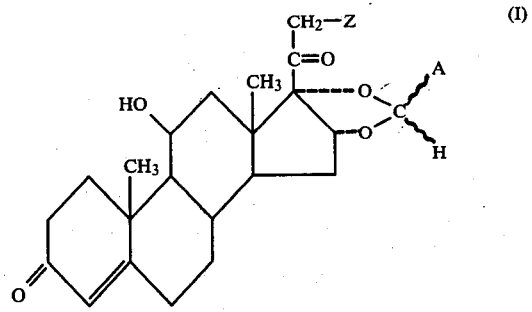

in the form of a stereoisomeric mixture or an epimer of the R or S type regarding the orientation of the substituents at the carbon atom in position 22, in which formula A is n-propyl or n-butyl and Z is hydroxyl or hydroxyl esterified with a fatty acid with a straight or branched hydrocarbon chain having 1-5 carbon atoms.

The invention also refers to a process for the preparation of these compounds, a pharmaceutical preparation containing one of the compounds and a method for the treatment and control of inflammatory conditions.

22 Claims, No Drawings

4-PREGNENE-DERIVATIVES, A PROCESS FOR THEIR PREPARATION, COMPOSITION AND METHOD FOR THE TREATMENT OF INFLAMMATORY CONDITIONS

DESCRIPTION

Technical Field

The present invention relates to novel, pharmacologically active compounds, a process for their preparation including the separation of the obtained stereoisomeric mixture into its separate components (diastereoisomers). The invention also relates to pharmaceutical compositions containing the compounds and to methods of treatment of inflammatory conditions with these compounds.

The object of the invention is to provide a steroid compound which possesses a combination of high anti-inflammatory potency on the place of application and low glucocorticoid systemic effects.

Background Art

It is known that certain glucocorticoids can be used for topical treatment of inflammatory and allergic conditions in the skin and respiratory airways and for injection therapy at diseases of the joints. The Swedish Pat. No. 378 110 discloses anti-inflammatory active stereoisomeric components of a stereoisomeric mixture of a steroid having the general formula:

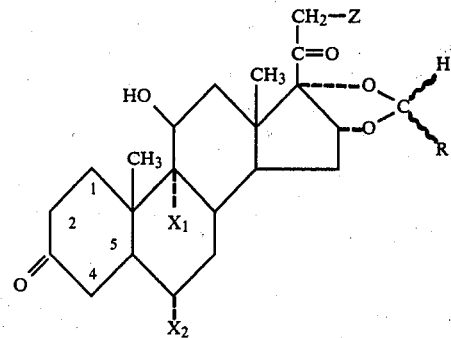

wherein the 1,2 and 4,5-positions are saturated or a double bond present in at least one of said two positions, $X_1$ and $X_2$ are the same or different and selected among hydrogen and fluorine, Z is hydroxyl or esterified hydroxyl and R is an alkyl group with straight or branched hydrocarbon chains having 1-10 carbon atoms.

The disclosure in Swedish Pat. No. 378 110 of compounds of the above formula wherein position, 4,5 but not 1,2 consists of a double bond is restricted to the stereoisomeric components of the compound of the formula

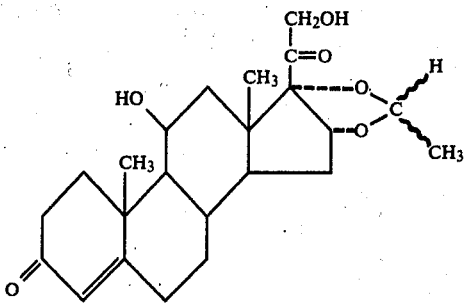

Test results disclosed elsewhere in this specification demonstrate that the stereoisomeric component R of this compound does not comply with the object of the present invention.

Disclosure of the Invention

The present invention is based on the observation that certain unsymmetrical 16,17-acetals of 16α-hydroxycortisol possess a high anti-inflammatory potency on the place of application in combination with low glucocorticoid systemic effects. The compounds of the invention can be used for the treatment and control of severe inflammatory conditions.

The compounds of the invention are characterized by the formula

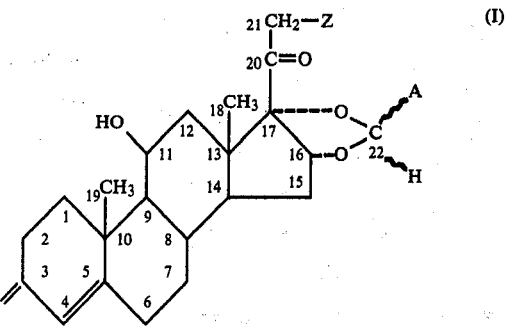

wherein A is n-propyl or n-butyl and Z is hydroxyl or hydroxyl esterified with a fatty acid with a straight or branched hydrocarbon chain having 1-5 carbon atoms.

The individual stereoisomeric components present in a mixture of a steroid having the above formula (I) can be elucidated in the following way:

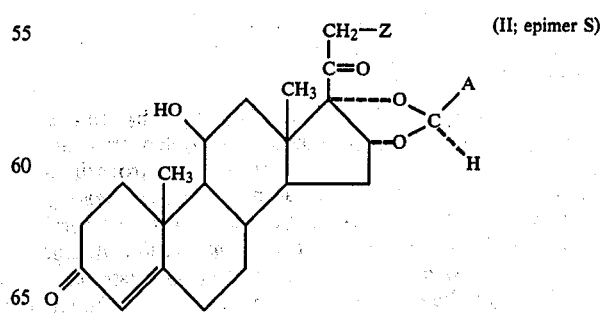

and

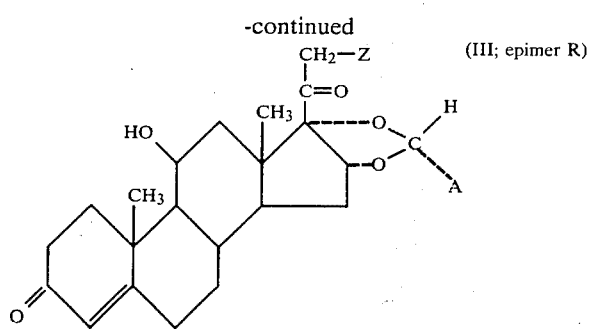

(III; epimer R)

Diastereoisomers like II and III, in which the configuration differs only at one (C-22) out of several asymmetric carbon atoms are denoted epimers.

By a comparison of the chemical and physical properties, for instance the chromatographic behaviour, specific optical rotation and spectroscopic properties in $^1$H-NMR and masspectrometry between the epimers of the compounds of the invention and the epimers of an analogous compound for which the configuration is known, it has been possible to deduce the configurations of the former compounds. Such a comparison has been made with the epimers of budesonide for which the configuration is unambiguously established, cf. Acta Cryst. (1978), B 34, 3027–3036.

The compounds of the invention are prepared by reaction of 16α-hydroxycortisol of the formula

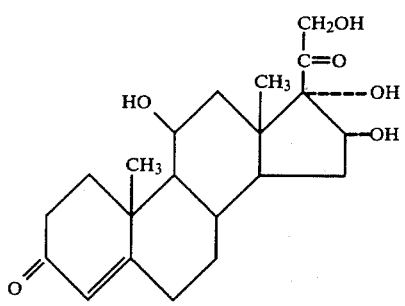

with an aldehyde of the formula

A-CHO or its acetals

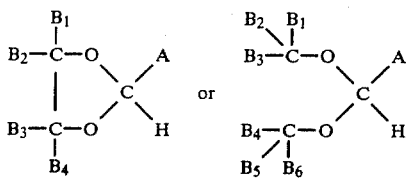

wherein A is n-propyl or n-butyl, and $B_1$ to $B_6$ are the same or different and each representing hydrogen or an alkyl group with straight or branched hydrocarbon chains having 1–10 carbon atoms, selected among methyl, ethyl, propyl, iso-propyl, butyl, iso-butyl, tert-butyl, pentyl, hexyl, heptyl, octyl, nonyl or decyl, e.g. acetals between n-butanal or n-pentanal and ethylene glycol, propylene glycol, 1,2-butanediol, 1,2-pentanediol, 2,2,4-trimethyl-1,2-pentanediol, 2,3-hexanediol, 1,2-octanediol, methanol, ethanol, propanol, iso-propanol, butanol, isobutanol, tert-butanol, pentanol, hexanol, heptanol, diethylisopropylcarbinol and 2,2,5,5-tetramethylhexanol-3.

If an 21-ester is desired, the obtained product is esterified.

The esterification is performed with a fatty acid with a straight or branched hydrocarbon chain having 1–5 carbon atoms. The fatty acid can for instance be acetic acid, butyric acid or trimethyl acetic acid.

The reaction between 16α-hydroxycortisol and the aldehyde or the acetal is suitably carried out by adding the steroid to a solution of the aldehyde or the acetal together with an acid catalyst e.g. perchloric acid, p-toluene sulphonic acid, hydrochloric acid etc. in dioxane or equivalent solvents, the reaction mixture being then taken up in methylene chloride and neutralized. The crude steroid acetal derivative formed, which is composed of a mixture of the 22R- and 22S-epimers, is after isolation purified by chromatography on a suitable material, for instance crosslinked dextran gels of Sephadex ® LH-type with suitable solvents as eluants, e.g. halogenated hydrocarbons, ethers, esters such as ethyl acetate or acetonitrile.

To prepare the 21-acyloxy derivatives the free acid, its halide or anhydride may be used in the esterification reaction.

The individual R and S epimers, which are formed at the reaction, possess practically identical solubility characteristics. Accordingly, they have turned out to be impossible to separate and isolate from the epimeric mixture by conventional methods for resolution of stereoisomers, e.g. fractionated crystallization. The process according to the invention consists in subjecting stereoisomeric mixtures according to the formula (I) above to column chromatography, the epimers R and S being separated in view of different mobility on the stationary phase, why they can be separately recovered. The chromatography may be carried out for instance on cross-linked dextran gels of the type Sephadex ® LH, e.g. Sephadex ® LH-20 in combination with a suitable organic solvent as eluting agent. Sephadex ® LH-20, prepared by Pharmacia Fine Chemicals AB, Uppsala, Sweden, is a bead-formed hydroxypropylated dextran gel wherein the dextran chain are cross-linked to give a three-dimensional polysaccharide network. As eluting agent a mixture of n-heptane-chloroform-ethanol in the proportions 0–50:50–100:10-1 has successfully been used, preferably a 20:20:1 mixture.

The epimers R and S with the general formulas (II) and (III) respectively above, wherein Z is hydroxyl, can also be obtained from a stereoisomeric mixture with the general formula (I) above, wherein Z is hydroxyl esterified with a fatty acid, after resolution by chromatography on Sephadex ® LH-20 together with a suitable solvent or mixture of solvents, e.g. n-heptane-chloroform-ethanol in the proportions 0–50:50–100:10-1, preferably 20:20:1, as mobile phase. The separated and isolated epimers R and S with the general formula (II) and (III) respectively above, wherein Z is hydroxyl esterified with a fatty acid, may be, if so desired, submitted to base catalyzed hydrolysis, with hydroxides, carbonates or hydrogen carbonates of alkaline metals, e.g. sodium or potassium hydroxide, sodium or potassium carbonate or sodium or potassium hydrogen carbonate, to give the epimers R and S, wherein Z is hydroxyl.

The compounds of the invention may be used for different modes of local administration dependent on the site of inflammation, e.g. percutaneously, parenterally or for local administration in the respiratory airways by inhalation. An important aim of the formulation design is to reach optimal bioavailability of the active steroid ingredient. For percutaneous formulations this is advantageously achieved if the steroid is dissolved with a high thermodynamic activity in the vehicle. This is attained by using a suitable system of solvents comprising suitable glycols, such as propylene glycol or 1,3-butanediol either as such or in combination with water.

It is also possible to dissolve the steroid either completely or partially in a lipophilic phase with the aid of a surfactant as a solubilizer. The percutaneous compositions can be an ointment, an oil in water cream, a water in oil cream or a lotion. In the emulsion vehicles the system comprising the dissolved active component can make up the disperse phase as well as the continuous one. The steroid can also exist in the above compositions as a micronized, solid substance.

Compressed aerosols for steroids are intended for oral or nasal inhalation. The aerosol system is designed in such a way that each delivered dosage contains 100–1000 μg, preferably 20–250 μg of the active steroid. The most active steroids are administered in the lower part of the dosage range. The micronized steroid consists of particles substantially smaller than 5 μm, which are suspended in a propellant gas mixture with the assistance of a dispersant, such as sorbitan trioleate, oleinic acid, lecithin or sodium salt of dioctylsulphosuccinic acid.

Working Examples

The invention will be further illustrated by the following non-limitative examples. In the examples a flow-rate of 2.5 ml/cm$^2$.h$^{-1}$ is used at the preparative chromatographic runs. Molecular weights are in all examples determined with mass spectrometry and the melting points on a Leitz Wetzlar hot stage microscope. All HPLC analyses (HPLC=High Performance Liquid Chromatography) were performed on a Waters μBondapak C$_{18}$ column (300×3.9 mm internal diameter) with a flow-rate of 1.0 ml/min and with ethanol/water in ratios between 42:58 and 52:48 as mobile phase.

EXAMPLE 1

16α,17α-[22R,S]-Propylmethylenedioxy-4-pregnene-11β,21-diol-3,20-dione

To a solution of 125 mg of freshly distilled n-butanal and 0.1 ml of 72% perchloric acid in 20 ml thoroughly purified and dried dioxane 500 mg of 16α-hydroxycortisol were added in portions for 15 minutes while stirring. The reaction mixture was then allowed to stand for further 5 hours at room temperature under stirring, and then diluted with 100 ml of methylene chloride. The solution was washed with a potassium carbonate solution (10% in water) and water and was then dried and evaporated in vacuo. The residue was chromatographed on a column (77×6.3 cm internal diameter) packed with Sephadex ® LH-20 using chloroform as eluant. The fraction 1995–2235 ml was collected and evaporated. The residue was dissolved in methylene chloride and precipitated with petroleum ether. 446 mg (89%) of 16α,17α-[22R,S]-propylmethylenedioxy-4-pregnene-11β,21-diol-3,20-dione was obtained. HPLC-analysis showed 99.2% purity and the ratio 47:53 between the 22S- and 22R-epimers. The product had the following properties: Melting point: 175°–203° C.; $[\alpha]_D^{25} = +138.0°$ (c=0.198; CH$_2$Cl$_2$); molecular weight: 432 (calculated 432.6).

EXAMPLE 2

16α,17α-[22R,S]-Propylmethylenedioxy-4-pregnene-11β,21-diol-3,20-dione

To a solution of 118 mg n-butanal diethylacetal and 0.1 ml of 72% perchloric acid in 25 ml of thoroughly purified and dried dioxane 200 mg of 16α-hydroxycortisol were added in portions for 15 minutes. The reaction mixture was then allowed to stand at room temperature for further 5 hours. By working up according to the procedure in Example 1 214 mg of crude product was obtained. This product was chromatographed on a column (83×2.5 cm internal diameter) packed with Sephadex ® LH-20 using chloroform as eluant. The fraction 365–455 ml was collected and evaporated. The residue was further purified by chromatography on a Sephadex ® LH-20 column (85×2.5 cm) using a mixture of n-heptane-chloroform-ethanol (20:20:1) as the eluant. The fraction 855–1010 ml was collected and evaporated. The residue was dissolved in methylene chloride and precipitated with petroleum ether giving 152 mg (67%) of 16α,17α-[22R,S]-propylmethylenedioxy-4-pregnene-11β,21-diol-3,20-dione. HPLC-analysis showed 98.2% purity and the ratio 43:57 between the 22S- and 22R-epimers. Molecular weight: 432 (calculated 432.6).

EXAMPLE 3

16α,17α-[22R,S]-Propylmethylenedioxy-11β-hydroxy-21-acetoxy-4-pregnene-3,20-dione To a solution of 918 mg of 16α,17α-[22R,S]-propylmethylenedioxy-4-pregnene-11β,21-diol-3,20-dione in 60 ml of pyridine a solution of 460 mg acetyl chloride in 30 ml of dioxane was added dropwise while stirring. The reaction mixture was allowed to stand over night at room temperature and then diluted with 500 ml of methylene chloride, washed with sodium carbonate solution (5% in water), water and dried. After evaporation in vacuo the residue was chromatographed on a column (72×6.3 cm internal diameter) packed with Sephadex ® LH-20 using chloroform as eluant. The fraction 1275–1695 ml was collected, evaporated and precipitated with methylene chloride-petroleum ether. 671 mg (67%) of 16α,17α-[22R,S]-propylmethylenedioxy-11β-hydroxy-21-acetoxy-4-pregnene-3,20-dione was obtained. HPLC-analysis showed 99% purity and the ratio 53:47 between the 22S- and 22R-epimers. The product had the following properties: Melting point: 118°–137° C.; $[\alpha]_D^{25} = +125.0°$ (c=0.200; CH$_2$Cl$_2$); molecular weight: 474 (calculated 474.6).

EXAMPLE 4

16α,17α-[22S]- and 16α,17α-[22-R]-propylmethylenedioxy-11β-hydroxy-21-acetoxy-4-pregnene-3,20-dione 16α,17α-[22R,S]-Propylmethylenedioxy-11β-hydroxy-21-acetoxy-4-pregnene-3,20-dione (40 mg) was chromatographed on a column (75×6.3 cm internal diameter) packed with Sephadex ® LH-20 using n-heptane-chloroform-ethanol (20:20:1) as eluant. The fractions 1530–1680 ml and 1681–1860 ml were collected and evaporated. The two products were precipitated from methylene chloride-petroleum ether. The product from the first fraction (16.5 mg) was identified with the aid of $^1$H-NMR and mass spectrometry to be the 22S-epimer and the product from the latter fraction (13.0 mg) in the same way as the 22R-epimer. The epimers had the following properties. Epimer S: Melting point 176°–79° C.; $[\alpha]_D^{25}= +107.3°$ (c=0.262; CH$_2$Cl$_2$); molecular weight: 474 (calculated 474.6). Epimer R: Melting point 112°–17° C.; $[\alpha]_D^{25}= +132.2°$ (c=0.152; CH$_2$Cl$_2$); molecular weight: 474 (calculated 474.6). The purity of the epimers was determined by HPLC-analysis to be 99.7% for the S-epimer and 95.0% for the R-epimer. 4% of the impurities of the R-epimer consists of epimer S.

EXAMPLE 5

16α,17α-[22R,S]-Propylmethylenedioxy-11β-hydroxy-21-butyryloxy-4-pregnene-3,20-dione To a solution of 100 mg of 16α,17α-[22R,S]-propylmethylenedioxy-4-pregnene-11β,21-diol-3,20-dione in 5 ml of pyridine a solution of 70 mg of butyryl chloride in 3 ml of dioxane was added dropwise. The reaction and isolation procedures for the crude product were performed as in Example 2. The crude product was chromatographed on a column (80×2.5 cm internal diameter) packed with Sephadex ® LH-20 using chloroform as eluant. The fraction 200–250 ml was collected, evaporated and precipitated from methylene chloride-petroleum ether. 70 mg (60%) of 16α,17α-[22R,S]-propylmethylenedioxy-11β-hydroxy-21-butyryloxy-4-pregnene-3,20-dione was obtained. HPLC-analysis showed 99.7% purity and the ratio 44:56 between the 22S- and 22R-epimers. The product has the following properties: Melting point: 64°–75° C.; $[\alpha]_D^{25}= +121.0°$ (c=0.218; CH$_2$Cl$_2$); molecular weight: 502 (calculated 502.6).

EXAMPLE 6

16α,17α-[22R,S]-Propylmethylenedioxy-11β-hydroxy-21-pivalyloxy-4-pregnene-3,20-dione To a solution of 100 mg of 16α,17α-[22R,S]-propylmethylenedioxy-4-pregnene-11β,21-diol-3,20-dione in 5 ml of pyridine a solution of 65 mg of trimethylacetyl chloride in 3 ml of dioxane was added dropwise. The reaction and isolation procedures for the crude product were performed as in Example 2. The crude product was chromatographed on a column (73×6.3 cm internal diameter) packed with Sephadex ® LH-20 using chloroform as eluant. The fraction 1245–1485 ml was collected, evaporated and precipitated from methylene chloride-petroleum ether. 73 mg (61%) of 16α,17α-[22R,S]-propylmethylenedioxy-11β-hydroxy-21-pivalyloxy-4-pregnene-3,20-dione was obtained. HPLC-analysis showed 98.7% purity and the ratio 46:54 between the 22S- and 22R-epimers. The product had the following properties. Melting point: 95°–105° C.; $[\alpha]_D^{25}= +115.5°$ (c=0.110; CH$_2$Cl$_2$); molecular weight: 516 (calculated 516.7).

EXAMPLE 7

16α,17α-[22R,S]-Butylmethylenedioxy-4-pregnene-11β,21-diol-3,20-dione

To a solution of 170 mg of n-pentanal and 0.3 ml of perchloric acid (72%) in thoroughly purified and dried dioxane 500 mg of 16α-hydroxycortisol were added in portions for 15 minutes. The reaction mixture was then allowed to stand at room temperature for further 5 hours. By working up according to the procedure in Example 1 590 mg of crude product was obtained. This product was chromatographed on a column (73×6.3 cm internal diameter) packed with Sephadex ® LH-20 using chloroform as eluant. The fraction 1860–2400 ml was collected and evaporated. The residue was dissolved in methylene chloride and precipitated from petroleum ether. 513 mg (87%) of 16α,17α-[22R,S]-butylmethylenedioxy-4-pregnene-11β,21-diol-3,20-dione was obtained. HPLC-analysis showed 98.9% purity and the ratio 50:50 between the 22S- and 22R-epimers. The product had the following properties. Melting point: 154°–60° C.; $[\alpha]_D^{25}= +129.6°$ (c=0.308; CH$_2$Cl$_2$); molecular weight 446 (calculated 446.6).

EXAMPLE 8

16α,17α-[22R,S]-Butylmethylenedioxy-4-pregnene-11β,21-diol-3,20-dione

To a solution of 58 mg of n-pentanal propylene acetal and 0.1 ml of 72% perchloric acid in 25 ml of thoroughly purified and dried dioxane 100 mg of 16α-hydroxycortisol were added in portions for 15 minutes. The reaction mixture was then allowed to stand at room temperature for further 5 hours and worked up according to the procedure in Example 1. The crude product was chromatographed on a column (83×2.5 cm internal diameter) packed with Sephadex ®LH-20 using chloroform as the eluant. The fraction 285–380 ml was collected and evaporated. This product was further purified by chromatography on a Sephadex ®LH-20 column (85×2.5 cm) using n-heptane-chloroform-ethanol (20:20:1) as the eluant. The fraction 735–915 ml was collected and evaporated. The residue was dissolved in methylene chloride and precipitated with petroleum ether giving 77 mg (64%) of 16α,17α-[22R,S]-butylmethylenedioxy-4-pregnene-11β,21-diol-3,20 dione. HPLC-analysis showed 96.8% purity and the ratio 46:54 between the 22S- and 22R-epimers. Molecular weight: 446 (calculated 446.6).

EXAMPLE 9

16α,17α-[22S]- and 16α,17α-[22R]-butylmethylenedioxy-4-pregnene-11β,21-diol-3,20-dione 16α,17α-[22R,S]-Butylmethylenedioxy-4-pregnene-11β,21-diol-3,20-dione (500 mg) was chromatographed on a column (76×6.3 cm internal diameter) packed with Sephadex ® LH-20 using n-heptane-chloroform-ethanol (20:20:1) as eluant. The fractions 4050–4395 ml and 4771–4950 ml were collected and evaporated. The two products were precipitated from methylene chloride-petroleum ether. The products were identified with the aid of $^1$H-NMR and mass spectrometry as the S-epimer (79 mg) and R-epimer (127 mg), respectively. The purity of the epimers was determined by HPLC-analysis to be 97.3% (contains 2.1% of the R-epimer) for the S-epimer and 97.9% (contains 0.5% of the S-epimer) for the R-epimer. The epimers had the following properties. Epimer S: Melting point 165°–71° C.; $[\alpha]_D^{25}= +119.9°$ (c=0.382; CH$_2$Cl$_2$); molecular weight 446 (calculated 446.6). Epimer R: Melting point 154°–62° C.; $[\alpha]_D^{25}= +148.3°$ (c=0.302; CH$_2$Cl$_2$); molecular weight 446 (calculated 446.6).

EXAMPLE 10

16α,17α-[22R,S]-Butylmethylenedioxy-11β-hydroxy-21-acetoxy-4-pregnene-3,20-dione 16α,17α-[22R,S]-Butylmethylenedioxy-4-pregnene-11β,21-diol-3,20-dione (658 mg) and acetic anhydride (5 ml) were dissolved in 5 ml of pyridine and was left over night at room temperature. The reaction mixture was then poured into ice water and extracted several times with methylene chloride. The combined extracts were in turn washed with diluted hydrochloric acid (1%), sodium carbonate (5% in water), saturated sodium chloride solution, dried and evaporated in vacuo. The residue was chromatographed on a column (73×6.3 cm internal diameter) packed with Sephadex® LH-20 using chloroform as eluant. The fraction 1215–1455 ml was collected and evaporated. The residue was dissolved in methylene chloride and precipitated from petroleum ether. 507 mg (71%) of 16α,17α-[22R,S]-butylmethylenedioxy-11β-hydroxy-21-acetoxy-4-pregnene-3,20-dione was obtained. HPLC-analysis showed 98.5% purity and the ratio 51:49 between the 22S- and the 22R-epimers. The product had the following properties: Melting point: 108°–25° C.; $[\alpha]_D^{25} = +126.5°$ (c=0.238; $CH_2Cl_2$); molecular weight 488 (calculated 488.6).

EXAMPLE 11

16α,17α-[22S]- and 16α,17α-[22R]-butylmethylenedioxy-11β-hydroxy-21-acetoxy-4-pregnene-3,20-dione 16α,17α-[22R,S]-Butylmethylenedioxy-11β-hydroxy-21-acetoxy-4-pregnene-3,20-dione (485 mg) was chromatographed according to the procedure described in Example 3. The fractions 1275–1425 and 1486–1590 were collected and evaporated. The two products were precipitated from methylene chloride-petroleum ether. The products were identified with the aid of $^1$H-NMR and mass spectrometry as the S-epimer (140 mg) and the R-epimer (204 mg), respectively. The purity of the epimers was determined by HPLC-analysis to be 97.5% (contains 1.3% of the R-epimer) for the S-epimer and 97.1% (contains 1.2% of the S-epimer) for the R-epimer. The epimers had the following properties. Epimer S: Melting point 153°–57° C.; $[\alpha]_D^{25} = +104.4°$ (c=0.226; $CH_2Cl_2$); molecular weight 488 (calculated 488.6). Epimer R: Melting point 75°–77° C.; $[\alpha]_D^{25} = +140.4°$ (c=0.228; $CH_2Cl_2$); molecular weight 488 (calculated 488.6).

EXAMPLE 12

16α,17α-[22S]-Butylmethylenedioxy-4-pregnene-11β,21-diol-3,20-dione

To a solution of 16α,17α-[22S]-butylmethylenedioxy-11β-hydroxy-21-acetoxy-4-pregnene-3,20-dione (53 mg) in 10 ml of methanol 1.5 ml of potassium carbonate (10% in water) was added. After stirring for 10 minutes at room temperature in nitrogen atmosphere the reaction mixture was neutralized with acetic acid, diluted with 25 ml of water and extracted with methylene chloride. The combined extracts were dried and evaporated in vacuo. The residue was chromatographed on a column (83×2.5 cm internal diameter) packed with Sephadex® LH-20 using chloroform as eluant. The fraction 285–330 ml was collected and evaporated giving 35 mg (73%) of 16α,17α-[22S]-butylmethylenedioxy-4-pregnene-11β,21-diol-3,20-dione after precipitation from methylene chloride-petroleum ether. This product was identified by mass spectrometry and its purity was shown by HPLC-analysis to be 98.8% (contains 0.8% of the R-epimer). Its melting point was 160°–67° C., $[\alpha]_D^{25} = +115.0°$ (c=0.332; $CH_2Cl_2$) and molecular weight 446 (calc. 446.6).

EXAMPLE 13

16α,17α-[22R]-Butylmethylenedioxy-4-pregnene-11β,21-diol-3,20-dione

To a solution of 16α,17α-[22R]-butylmethylenedioxy-11β-hydroxy-21-acetoxy-4-pregnene-3,20-dione (58 mg) in 10 ml of methanol 1.5 ml of potassium carbonate (10% in water) was added. The reaction mixture was treated as in Example 10. The crude product was chromatographed on a column (83×2.5 cm internal diameter) packed with Sephadex® LH-20 using chloroform as eluant. The fraction 305–360 ml was collected and evaporated giving 43 mg (81%) of 16α,17α-[22R]-butylmethylenedioxy-4-pregnene-11β,21-diol-3,20-dione after precipitation from methylene chloride-petroleum ether. The product was identified by mass spectrometry and its purity was shown by HPLC-analysis to be 95.4% (contains 2.5% of the S-epimer). Its melting point was 152°–62° C., $[\alpha]_D^{25} = +149.0°$ (c=0.312; $CH_2Cl_2$) and molecular weight 446 (calc. 446.6).

EXAMPLE 14

Pharmaceutical preparations

The following non-limitative examples illustrate formulations intended for different topical forms of administration. The amount of active steroid in the percutaneous formulations are ordinarily 0.001–0.2% (w/w), preferably 0.01–0.1% (w/w).

| Formulation 1, Ointment | |
| --- | --- |
| Steroid, micronized | 0.025 g |
| Liquid paraffin | 10.0 g |
| White soft paraffin | ad 100.0 g |
| Formulation 2, Ointment | |
| Steroid | 0.025 g |
| Propylene glycol | 5.0 g |
| Sorbitan sesquioleate | 5.0 g |
| Liquid paraffin | 10.0 g |
| White soft paraffin | ad 100.0 g |
| Formulation 3, Oil in water cream | |
| Steroid | 0.025 g |
| Cetanol | 5.0 g |
| Glyceryl monostearate | 5.0 g |
| Liquid paraffin | 10.0 g |
| Cetomacrogol 1000 | 2.0 g |
| Citric acid | 0.1 g |
| Sodium citrate | 0.2 g |
| Propylene glycol | 35.0 g |
| Water | ad 100.0 g |
| Formulation 4, Oil in water cream | |
| Steroid, micronized | 0.025 g |
| White soft paraffin | 15.0 g |
| Liquid paraffin | 5.0 g |
| Cetanol | 5.0 g |
| Sorbimacrogol stearate | 2.0 g |
| Sorbitan monostearate | 0.5 g |
| Sorbic acid | 0.2 g |
| Citric acid | 0.1 g |
| Sodium citrate | 0.2 g |
| Water | ad 100.0 g |
| Formulation 5, Water in oil cream | |
| Steroid | 0.025 g |
| White soft paraffin | 35.0 g |
| Liquid paraffin | 5.0 g |
| Sorbitan sesquioleate | 5.0 g |

| -continued | |
|---|---|
| Sorbic acid | 0.2 g |
| Citric acid | 0.1 g |
| Sodium citrate | 0.2 g |
| Water | ad 100.0 g |
| Formulation 6, Lotion | |
| Steroid | 0.25 mg |
| Isopropanol | 0.5 ml |
| Carboxyvinylpolymer | 3 mg |
| NaOH | q.s. |
| Water | ad 1.0 g |
| Formulation 7, Suspension for injection | |
| Steroid, micronized | 0.05-10 mg |
| Sodium carboxymethylcellulose | 7 mg |
| NaCl | 7 mg |
| Polyoxyethylene (20) sorbitan monooleate | 0.5 mg |
| Phenyl carbinol | 8 mg |
| Water, sterile | ad 1.0 ml |
| Formulation 8, Aerosol for oral and nasal inhalation | |
| Steroid, micronized | 0.1% w/w |
| Sorbitan trioleate | 0.7% w/w |
| Trichlorofluoromethane | 24.8% w/w |
| Dichlorotetrafluoromethane | 24.8% w/w |
| Dichlorodifluoromethane | 49.6% w/w |
| Formulation 9, Solution for atomization | |
| Steroid | 7.0 mg |
| Propylene glycol | 5.0 g |
| Water | ad 10.0 g |

Pharmacological Tests

All steroids according to the present invention are physiologically active compounds. The glucocorticoid properties of the compounds have been compared with those of budesonide (16α,17α-[22R,S]-propylmethylenedioxypregna-1,4-diene-11β,21-diol-3,20-dione), as this compound is one of the glucocorticoids which today has reached most far towards the desired combination of local and systemic effects (Thalen and Brattsand, Arzneim.-Forsch. 29, 1687-1690 (1979)).

The topical anti-inflammatory activity has been investigated as the potency to prevent ear edema in rats according to the following procedure.

Ear edemas were induced on male rats weighing about 90 g by application of 20 μl/side of ear of 5% ethyl phenylpropiolate (Aldrich Co) dissolved in acetone. Two hours later the ear edema was measured with a special micrometer (Oditest, H. C. Kröplin, GmbH, Messzeug Fabrik). The glucocorticoids were applied as pretreatment 16 hours before induction of the edemas by application of 20 μl/side of ear in solutions of acetone (0.08-50 μg steroid/ml=0.0064-4 μg/rat). Six ears were tested per dose. The relative potency of the test compounds to prevent ear edemas was calculated with linear regression analysis in relation to the reference compound budesonide.

The potency of the compounds to induce systemic glucocorticoid effects has been investigated by s.c. injections as no systemic effects are attained with the dose levels used in the above mentioned topical test. 0.5 ml steroid preparation was injected into rats of the same sex and weight as above. At least 5 doses of each test compound were injected within the dose range 20-1280 μg/rat with 4 animals per dose. The body weight gain of the animals was determined during the first two days after injection and the thymus weight after two further days as these time intervals are the optimal ones for determination of the respective systemic effect. The relative potency of the compounds was calculated with linear regression analysis in relation to the reference substance budesonide. The results of the tests of the glucocorticoids of the invention in accordance with the procedure given above are shown in Table 1.

It is previously known that the introduction of a double bond into position 1,2 of cortisol will increase the glucocorticoid activity. Table 1 shows that the new compounds, which are 4-pregnene derivatives, quite surprisingly have approximately the same high topical anti-inflammatory activity as budesonide, a 1,4-pregnadiene derivative.

From Table 1 it can also be seen that the new compounds are 3-20 times less potent than budesonide to induce non-desirable systemic glucocorticoid effects. The new compounds also have 5-10 times higher anti-inflammatory potency than the previously known 16α,17α-[22R]-methylmethylenedioxy-4-pregnene-11β,21-diol-3,20-dione (Swedish patent no 378 110) while they are equally potent when comparing the systemic glucocorticoid activities.

To effectively safely treat severe inflammatory and allergic diseases of the skin, e.g. psoriasis and of the lung, e.g. asthma, there is a demand for compounds which possess a combination of high topical anti-inflammatory activity and a favourable ratio between this activity and the untoward systemic effects. The new compounds of this invention comply with these two claims at the same time.

TABLE 1
Pharmacological effects of tested compounds

| $C_a$—$C_b$ | A | Z | Epimer | Topical anti-inflammatory potency | Potency to induce systemic glucocorticoid actions | | Therapeutic ratio between topical potency and systemic potency | |
|---|---|---|---|---|---|---|---|---|
| | | | | | thymus involution | inhibition of body weight gain | topical/thymus involution | topical/body weight gain |
| —CH=CH— | $CH_3(CH_2)_2$ | OH | R + S[(1)] | 1 | 1 | 1 | 1 | 1 |
| —CH=CH— | $CH_3(CH_2)_2$ | OH | R | 1.70 | 2.04 | 1.61 | 0.8 | 1.1 |
| —$CH_2$—$CH_2$— | $CH_3$ | OH | R | 0.13 | 0.19 | 0.13 | 0.7 | 1.0 |
| —$CH_2$—$CH_2$— | $CH_3(CH_2)_2$ | OH | R + S[(1)] | 1.02 | 0.12 | 0.09 | 8.5 | 11.3 |
| —$CH_2$—$CH_2$— | $CH_3(CH_2)_2$ | $CH_3COO$ | R + S[(1)] | 0.68 | 0.16 | 0.09 | 4.3 | 7.6 |
| —$CH_2$—$CH_2$— | $CH_3(CH_2)_2$ | $CH_3COO$ | R | 1.15 | 0.16 | 0.06 | 7.2 | 19.2 |
| —$CH_2$—$CH_2$— | $CH_3(CH_2)_2$ | $CH_3(CH_2)_2COO$ | R + S[(1)] | 1.29 | 0.32 | 0.27 | 4.0 | 4.8 |
| —$CH_2$—$CH_2$— | $CH_3(CH_2)_2$ | $(CH_3)_3CCOO$ | R + S[(1)] | 1.00 | 0.29 | 0.19 | 3.5 | 5.3 |
| —$CH_2$—$CH_2$— | $CH_3(CH_2)_3$ | OH | R + S[(1)] | 1.11 | 0.07 | 0.05 | 15.9 | 22.2 |
| —$CH_2$—$CH_2$— | $CH_3(CH_2)_3$ | OH | R | 1.24 | 0.08 | 0.04 | 15.5 | 31.0 |
| —$CH_2$—$CH_2$— | $CH_3(CH_2)_3$ | $CH_3COO$ | R + S[(1)] | 0.82 | 0.14 | 0.17 | 5.9 | 4.8 |
| —$CH_2$—$CH_2$— | $CH_3(CH_2)_3$ | $CH_3COO$ | R | 1.09 | 0.12 | 0.16 | 9.1 | 6.8 |

[(1)]Ratio between epimer R and epimer S ≈ 1:1

We claim:

1. A compound of the formula

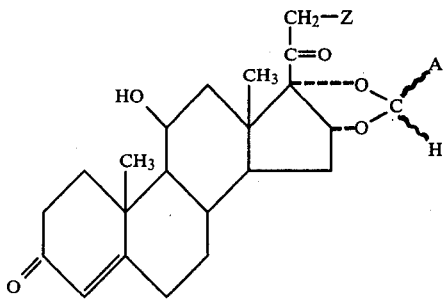

(I)

in the form of a stereoisomeric mixture or an epimer of the R or S type regarding the orientation of the substituents in the carbon atom at position 22, in which formula A is n-propyl or n-butyl and Z is hydroxyl or hydroxyl esterified with a fatty acid with a straight or branched hydrocarbon chain having 1–5 carbon atoms.

2. A steroid according to claim 1 wherein Z is hydroxyl and A is n-propyl or n-butyl.

3. A steroid according to claim 2 wherein A is n-propyl.

4. A steroid according to claim 3 in the form of the R-epimer.

5. A steroid according to claim 2 wherein A is n-butyl.

6. A steroid according to claim 5 in the form of the R-epimer.

7. A steroid according to claim 1 wherein Z is hydroxyl esterified with a straight or branched hydrocarbon chain having 1–5 carbon atoms and A is n-propyl or n-butyl.

8. A steroid according to claim 7 wherein A is n-propyl.

9. A steroid according to claim 8 wherein Z is hydroxyl esterified with acetic acid.

10. A steroid according to claim 9 in the form of the R-epimer.

11. A steroid according to claim 8 wherein Z is hydroxyl esterified with butyric acid.

12. A steroid according to claim 8 wherein Z is hydroxyl esterified with trimethylacetic acid.

13. A steroid according to claim 7 wherein A is n-butyl.

14. A steroid according to claim 13 wherein Z is hydroxyl esterified with acetic acid.

15. A steroid according to claim 14 in the form of the R-epimer.

16. A process for the preparation of a compound of the formula

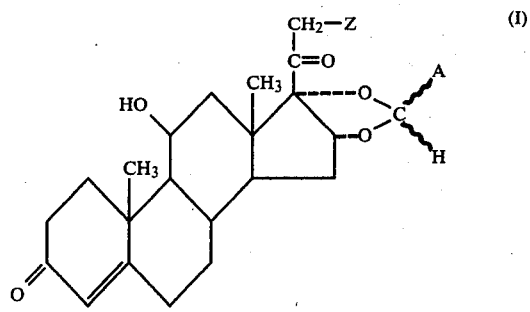

(I)

in the form of a stereoisomeric mixture or an epimer of the R or S type regarding the orientation of the substituents at the carbon atom in position 22, in which formula A is n-propyl or n-butyl and Z is hydroxyl, or hydroxyl esterified with a fatty acid with a straight or branched hydrocarbon chain having 1–5 carbon atoms, characterized by reacting 16α-hydroxycortisol of the formula

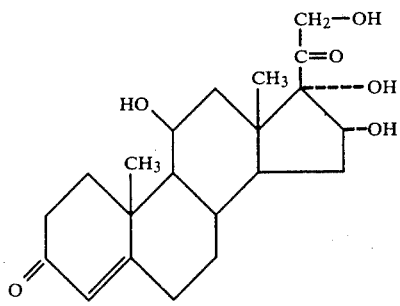

with an aldehyde of the formula

A-CHO or its acetals

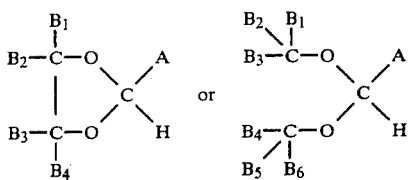

wherein A is defined as above and $B_1$–$B_6$ are the same or different and each representing hydrogen or an alkyl group with straight or branched hydrocarbon chains having 1–10 carbon atoms, whereafter if an 21-ester is desired Z is esterified with a fatty acid with a straight or branched hydrocarbon chain having 1–5 carbon atoms, and if an R epimer is desired submitting the obtained compound, before or after esterification to chromatography on a cross-linked dextran gel with an organic solvent as eluant.

17. A process according to claim 16 characterized in that a compound according to any of claims 2–15 is prepared.

18. A process according to claim 16 wherein the resolution of the stereoisomeric mixture into epimers of the R and S type regarding the orientation of the substituents at the carbon atom in position 22 is characterized by carrying out the chromatography on a bead-formed hydroxypropylated dextran gel wherein the dextran chains are cross-linked to give a three-dimensional polysaccharide network and using as eluting agent a mixture of n-heptane-chloroform-ethanol in the proportions 0–50:50–100:10-1.

19. A pharmaceutical preparation comprising as active ingredient a compound according to any of claims 1–15.

20. A pharmaceutical preparation according to claim 19 in dosage unit form.

21. A pharmaceutical preparation according to claims 19–20 comprising the active ingredient in association with a pharmaceutically acceptable carrier.

22. A method for the treatment and control of inflammatory conditions in mammals, including man, characterized by the administration to a host in need of such treatment of an effective amount of a compound according to any of claims 1–15.

* * * * *